(12) United States Patent
Grant et al.

(10) Patent No.: US 8,689,610 B2
(45) Date of Patent: Apr. 8, 2014

(54) INTEGRITY TEST METHOD FOR POROUS FILTERS

(75) Inventors: Donald C. Grant, Grand Marais, MN (US); Uwe Beuscher, Landenberg, PA (US); Scott Ross, Chestertown, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 231 days.

(21) Appl. No.: 12/888,714

(22) Filed: Sep. 23, 2010

(65) Prior Publication Data

US 2011/0067485 A1    Mar. 24, 2011

Related U.S. Application Data

(60) Provisional application No. 61/245,493, filed on Sep. 24, 2009.

(51) Int. Cl.
*G01N 15/08* (2006.01)

(52) U.S. Cl.
USPC .......................................................... 73/38

(58) Field of Classification Search
USPC .......................................................... 73/38
See application file for complete search history.

(56) References Cited

U.S. PATENT DOCUMENTS

| | | | |
|---|---|---|---|
| 5,064,529 A * | 11/1991 | Hirayama et al. | 210/90 |
| 5,507,959 A | 4/1996 | Glick | |
| 5,594,161 A | 1/1997 | Randhahn et al. | |
| 6,324,898 B1 | 12/2001 | Cote et al. | |
| 6,789,410 B1 | 9/2004 | Gupta et al. | |
| 6,938,460 B2 * | 9/2005 | Seiler et al. | 73/38 |
| 7,770,434 B2 | 8/2010 | Brüssermann et al. | |

FOREIGN PATENT DOCUMENTS

| | | |
|---|---|---|
| DE | 197 04 028 | 8/1998 |
| EP | 1 849 484 | 10/2007 |
| EP | 1849484 A1 * | 10/2007 |
| JP | 2005-13992 | 1/2005 |
| JP | 2006-068634 | 3/2006 |
| WO | WO 00/50158 | 8/2000 |

OTHER PUBLICATIONS

International Search Report and Written Opinion, Feb. 9, 2011, PCT/US2010/049965, 10 pages.
EPA Membrane Filtration Guidance Manual, Jun. 2003, pp. 4-29 to 4-37, EPA 815-D-03-008, United States Environmental Protection Agency, Washington, DC; USA.
"Predicting Log Removal Performance of Membrane Systems Using In-Situ Integrity Testing" vol. 35, Issue 1, Dec. 31, 1998, pp. 26-29.
People's of Republic of China Search Report, CN App No. 201080053183.3 dated Nov. 6, 2013.

\* cited by examiner

*Primary Examiner* — Hezron E Williams
*Assistant Examiner* — Gregory J Redmann
(74) *Attorney, Agent, or Firm* — Amy L. Miller (57) ABSTRACT

An improved method of testing the integrity of a porous filter is provided. The test method is an improvement over a gas-liquid diffusion test wherein the improvement comprises providing a conduit downstream of the filter and filling the conduit with a liquid, the conduit having a length to cross sectional area ratio selected to substantially resist diffusive flow of the gas through the liquid downstream of the filter material.

1 Claim, 9 Drawing Sheets

INTEGRITY TEST METHOD FOR POROUS FILTERS

RELATED APPLICATION

The present application is related to provisional application Ser. No. 61/245,493 filed Sep. 24, 2009.

BACKGROUND OF THE INVENTION

Porous materials such as membranes are used as filtration devices to eliminate undesirable contaminants from useful end products. Pharmaceutical, food processing and biotechnology industries require that the filtration devices comply with certain performance criteria. Integrity testing provides a means for ensuring that the device meets the desired performance criteria. With membrane filtration devices, integrity testing assures that the membrane is free of defects of a certain size, the presence of which would compromise device performance by allowing the end product to be contaminated.

One known integrity test method is the gas-liquid diffusion test, this test measures the flow of a gas through a liquid-wetted porous filter when the filtration device is pressurized on one side with the gas at a set pressure below the bubble point of the filter. If the device is free of defects, the measured flow rate of the gas will be relatively low at a given pressure, because the measured flow is primarily diffusive flow and not bulk gas flow. A device with defects however, will exhibit relatively large, bulk gas flow rates attributable to gas flowing through the defects in the porous filter.

For large multi-round housings with large porous filter areas, the diffusive flow through the filter material is often so high, however, that it cannot be distinguished from bulk flow attributable to small defects. Similarly, devices using extremely thin membranes such as those described in U.S. Pat. No. 7,306,729, have inherently high diffusive flow through the membrane which may make it difficult to recognize flow due to a defect. Therefore, the utility of the gas-liquid diffusion test for large filtration devices is limited. There exists a need for an integrity test method which provides increased sensitivity.

DETAILED DESCRIPTION OF THE INVENTION

The present invention relates to a method for testing the integrity of porous filter materials. More specifically, the inventive method provides enhanced sensitivity necessary for testing large area filters and filters with high diffusive flow rates. The method is simple, fast and may be easily integrated into an end user production environment.

Figure 1:
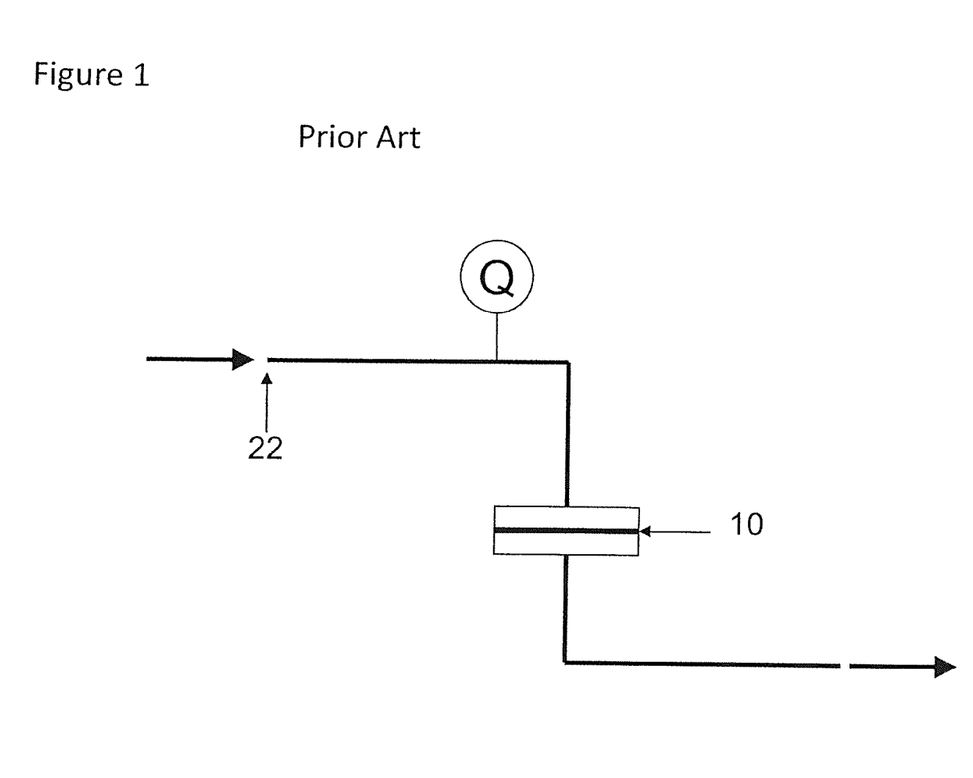
FIG. 1 is a schematic of the apparatus used in the gas-liquid diffusion test.

FIG. 1 depicts the standard gas-liquid diffusion test which is commonly used in the industry today to detect defects in filter media. The test measures the flow of a gas through a wetted porous filter (10). The porous filtration material of the filtration device is first wetted with a liquid. The wetting liquid is typically alcohol, water or other liquid. The system is pressurized on the inlet (22) side with gas, typically air or nitrogen. The gas flow on the inlet (22) side is measured at the test pressure.

The goal of the diffusion test is to measure the rate at which gas flows through the filter at a pressure below its bubble point. The bubble point of a filter is defined as the capillary pressure of the largest pores. The capillary pressure is dependent on the contact angle of the wetting liquid on the filter material, the surface tension of the wetting liquid, and the pore size and shape. At differential pressures below the bubble point, all pores of the filter should still be filled with the wetting liquid. During the diffusion test, any defects that are larger than the pores of the filter will de-wet and allow gas flow through the filter, which is measured.

If the gas flow measured in the diffusion test is less than the gas flow recommended by the filter manufacturer, the filtration device is considered to be free of defect. If the measured gas flow exceeds the diffusive gas flow recommended by the filter manufacturer, the filtration device is considered to be defective.

A significant shortcoming of the test is that when there is a gas pressure differential across a filter, gas on the high pressure side of the filter will absorb into the liquid in the filter, diffuse across the filter thickness, and desorb. This flow of gas across the filter interferes with the measurement of the gas flow through defects in the filter. The interference from this diffusive flow can be very large, especially for large area cartridges and thin membranes. For example, the diffusive flow rate across a cartridge at a differential pressure of 15 psi may be on the order of 20 cc/min for a typical filter cartridge.

The diffusive gas flow rate in the diffusion test is generally based on Fick's law which can be described using the equation given below:

$$Q = \frac{DH(\Delta P)AK}{L} \quad \text{(Equation 1)}$$

Q=Diffusive flow of gas across the porous filter, A=surface area of the porous filter, K=shape factor which is a function of porosity and tortuosity of the porous filter material, D=Diffusivity of gas in the wetting liquid, L=liquid path length and ΔP=pressure gradient across the porous filter. H=Henry's Law Constant.

In the above method, the path length, L, is defined by the thickness of wetting liquid in the porous filter. The path length is equal to the filter thickness if the filter is fully wetted with the wetting liquid. For thin porous filter materials, for example a filter material with a thickness less than about 50 microns, the liquid path length, L, is less than about 50 microns, thereby causing high diffusive gas flow, Q, during the test. This makes it difficult to make a distinction between bulk gas flow through a defect and diffusive gas flow, through the liquid in the membrane. For filtration devices with large surface area, A, of the porous filter, as described by Equation 1, the diffusive gas flow can also be high. This too makes it difficult to differentiate between diffusive flow and bulk gas flow due to one or more defects. The practical application of the gas-liquid diffusion test is therefore limited. The inventive integrity test method described below however shows a dramatic improvement in sensitivity over the gas-liquid diffusion test.

Figure 2:
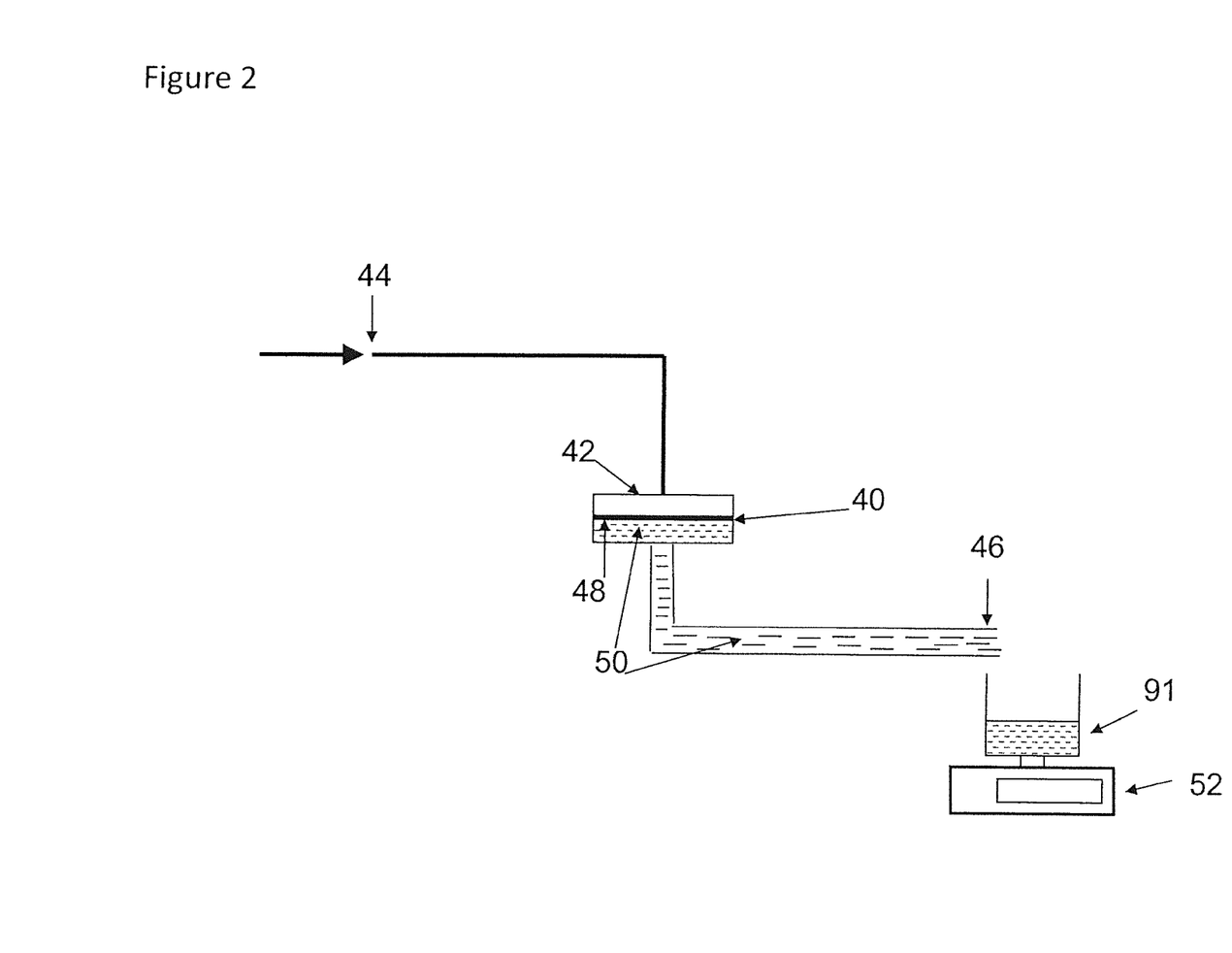
FIG. 2 is a schematic of the apparatus used to carry out the method according to an embodiment of the invention.

The apparatus used to carry out the method according to a first embodiment of the present invention is schematically illustrated in FIG. 2. The porous filter sample (40) in the form of either a flat disk or a pleated cartridge element is installed in a test fixture (42) between its inlet (44) and outlet (46). The sample is wetted with a wetting liquid by flushing the liquid through the sample for a certain duration. Preferably, the wetting liquid is chosen such that it does not adversely affect the membrane or the end-product. For a hydrophilic membrane, water or alcohol may be used as the wetting liquid. For a hydrophobic membrane, an alcohol solution, comprising isopropyl alcohol (IPA) or methanol may be used. The portion of the test fixture between the downstream side (48) of the sample and the outlet (46) is filled with the wetting liquid (50).

The sample is pressurized on the inlet (44) side with a gas (the gas may be air, nitrogen, or other gas). The gas pressure is slowly increased at a predetermined rate and the gas flow rate across the sample is measured by measuring the rate of liquid flow downstream of the sample. The rate of flow is measured by continuously monitoring the mass of the wetting liquid displaced using a balance (52) or another measuring device. In this embodiment of the invention, the effect of diffusional gas flow is essentially eliminated. The diffusing gas does not contribute significantly to a volume expansion of the downstream liquid column and will not lead to a liquid flow. Only gas bubbles resulting from gas moving through defects in the filter contribute to liquid displacement and result in a measured flow rate on the balance.

Figure 3:
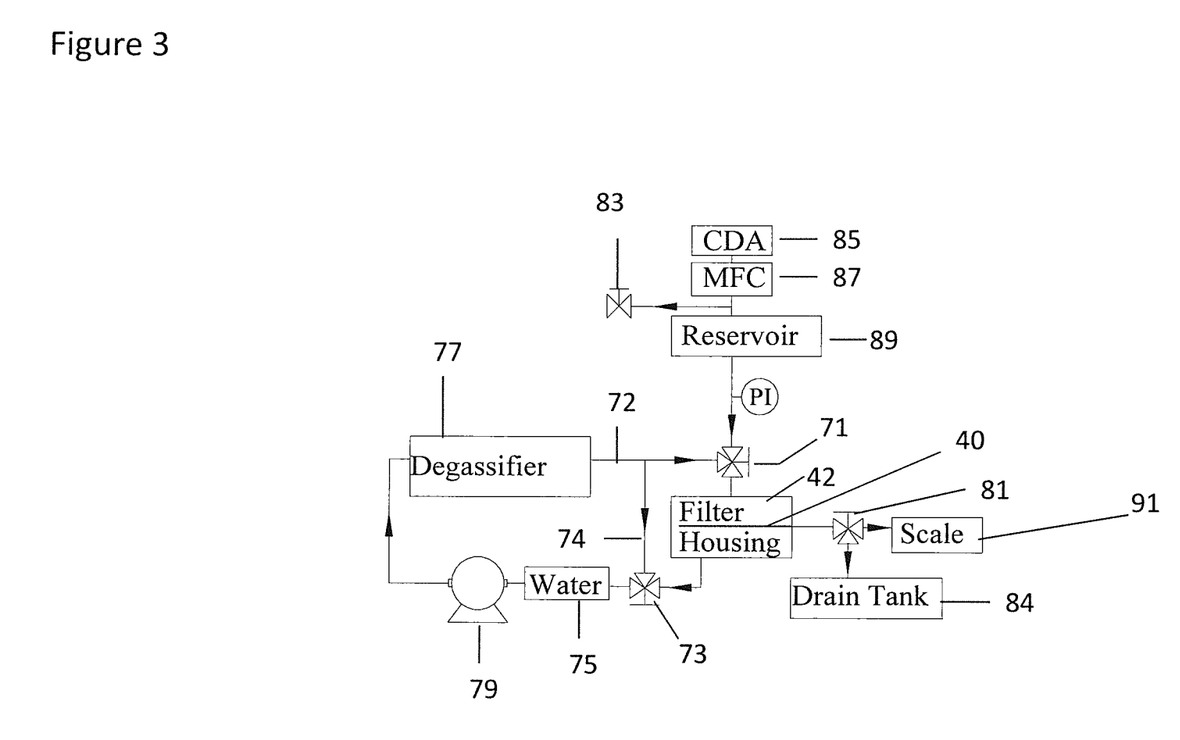
FIG. 3 is a schematic of the apparatus used to carry out the method according to an embodiment of the invention.
Figure 4:
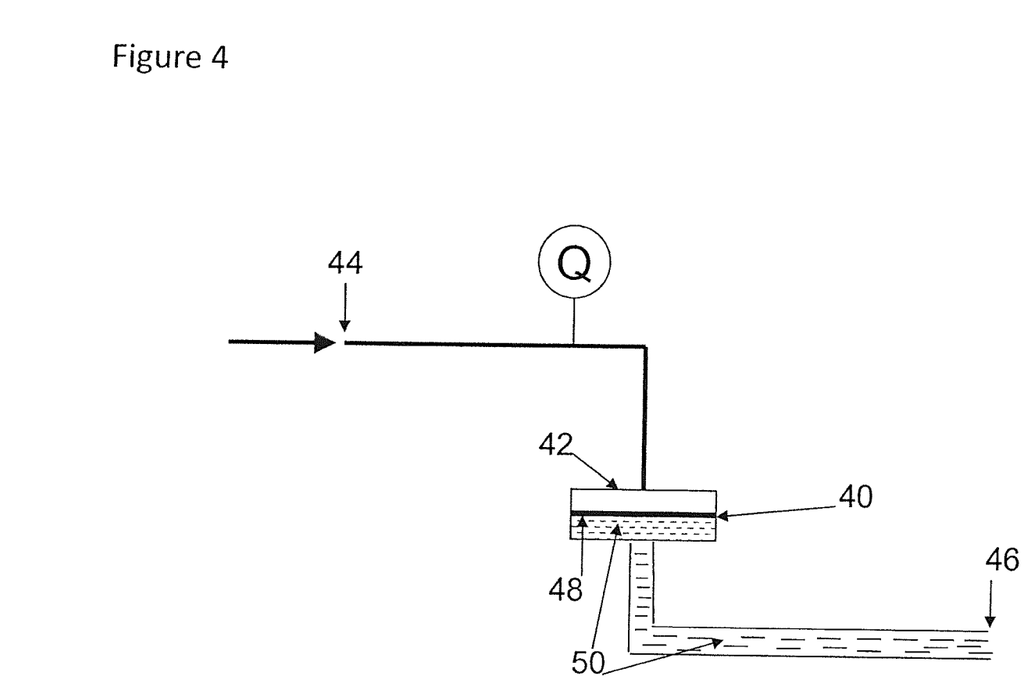
FIG. 4 is a schematic of the apparatus used to carry out the method according to an embodiment of the invention.

In an embodiment of the inventive test represented in FIG. 3, the porous filter media is first wetted with degassed water. This is done by setting the three-way valve (71) upstream of the filter to the water line (72) and the three way valve downstream of the filter (73) to the filter loop. Water is pumped by pump (79) from the water source (75) through both the degassifier (77) and the porous filter media (40). Although the schematic FIGS. 2, 3 and 4 depict the test apparatus configuration having the gas inlet above the filter and the liquid below, the fixture may be inverted so that the gas enters from the bottom of the fixture. This may be advantageous because it would prevent any gas that penetrates the membrane from accumulating on the membrane surface. After the porous filter media has been wetted, it is ready for testing.

The water flow to the porous filter media is stopped by setting the 3-way valve (73) on the water system to the bypass line (74) and opening the filter to the compressed dry air (CDA) line by adjusting the three-way valve (71) between the filter and the reservoir. Once the water flow to the filter has been stopped and the air line has been opened to the filter, the line going out from the filter is directed to the drain tank by setting three way valve (81) to the drain tank. This allows the water to be pushed out of the filter housing by compressed air without flooding the scale. After switching the outlet line to the drain tank, the system is ready for pressurization.

The valve (83) between the mass flow controller (MFC) and the reservoir is closed to begin pressurizing the system. As the pressure rises, it forces water out of the filter housing (42) and into the drain tank (84). When the water stops flowing, the outgoing line is switched from the drain tank to the scale (91) by adjusting the three way valve (81) to the scale.

Once the filter housing has drained and the outgoing line is switched to the scale, the actual test has begun. As the test progresses the scale reading rises very slowly for some time. Eventually, the mass on the scale begins to rise rapidly indicating that water is flowing out of the filter once again and the bubble point has been reached.

In another embodiment, the apparatus described in FIG. 2 is also used to carry out the method. In this embodiment, however instead of continuously increasing the pressure at a predetermined rate, the sample is pressurized on the upstream side and held at a constant pressure. The liquid flow rate is measured over time.

In another embodiment, the apparatus described in FIG. 2 is also used to carry out the method. In this embodiment, the pressure is increased incrementally and held constant for a defined period following each increase. The liquid flow rate is measured over time at each pressure. For example, the pressure could be incrementally increased by 0.5 psi every 5 minutes.

In another embodiment, the apparatus illustrated in FIG. 4 is used to carry out the invention. In this embodiment, the gas flow across the filter is measured upstream of the filter rather than measuring liquid flow rate downstream of the filter.

In this embodiment of the inventive method, the substantial increase in the liquid path length, L, as defined in Eq. (1), substantially reduces the diffusive gas flow, Q, through the sample. The reduction of diffusive flow improves the sensitivity of the integrity test method. For example, if L is made to be 1 cm rather than 50 µm (0.005 cm), the pathlength for diffusion is increased 200 fold; hence, diffusive flow is decreased 200 fold. The dimensions of the conduit may be selected such that the diffusive gas flow through the porous filter is substantially reduced. By reducing the diffusive component of gas flow, the sensitivity of the test is improved over that of a standard gas-liquid diffusion test.

The sensitivity of the filter integrity test method of the present invention may also be described using the Flow Ratio (FR). For a given pressure, FR may be defined as the ratio of flow measured using the inventive method to the diffusive flow measured using the standard gas-liquid diffusion test. FR has an inverse relationship to the sensitivity of the test method. For example, a flow ratio of 0.1 indicates an improvement in sensitivity of the inventive method over the standard gas-liquid diffusion test by a factor of 10. The dimensions of the conduit may be selected such that the increased sensitivity is by a factor of at least 2, preferably by a factor of at least 10 and most preferably by a factor of at least 100.

The inventive method may be used on a variety of filtration devices including, but not limited to flat membrane disks, pleated cartridges, stacked-disc cartridges, plate and frame cartridges, fluted sheet, tubing, fiber and spirally wound modules. The method is applicable to several polymeric membranes including a wide range of rated pore sizes. Examples of polymeric membranes include those made from Polytetrafluoroethylne (PTFE), Polyvinylidenefluoride (PVDF), Nylon, Polyethersulfone, Polyolefins, Polysulfone and Cellulose esters. The method may be used for both hydrophobic and hydrophilic membranes.

Example 1

The integrity test method of the present invention was carried out on an expanded PTFE (ePTFE) membrane made according to the teachings of U.S. Pat. No. 7,306,729. The membrane had an air flow of 2.6 Gurley secs and mass per area of 1.6 grams/m². A flat disk of this membrane, 47 mm in diameter was installed in a test fixture. The sample was wetted with IPA by circulating through the sample for about 5 minutes. As described in FIGS. 2 and 3, the portion of the test fixture between the downstream side of the sample and the outlet was filled with the wetting liquid IPA to create a liquid conduit.

After wetting the sample and filling downstream portions of the test apparatus with IPA, the sample was pressurized using air. Air pressure was slowly increased at a rate of 10 psi/min. The mass of IPA displaced was collected in a container and measured every second using a balance (Model CPA324S, Sartorius Corporation). The IPA flow rate was converted to volumetric gas flow rate by dividing the IPA mass flow rate by the density of IPA.

Figure 5:
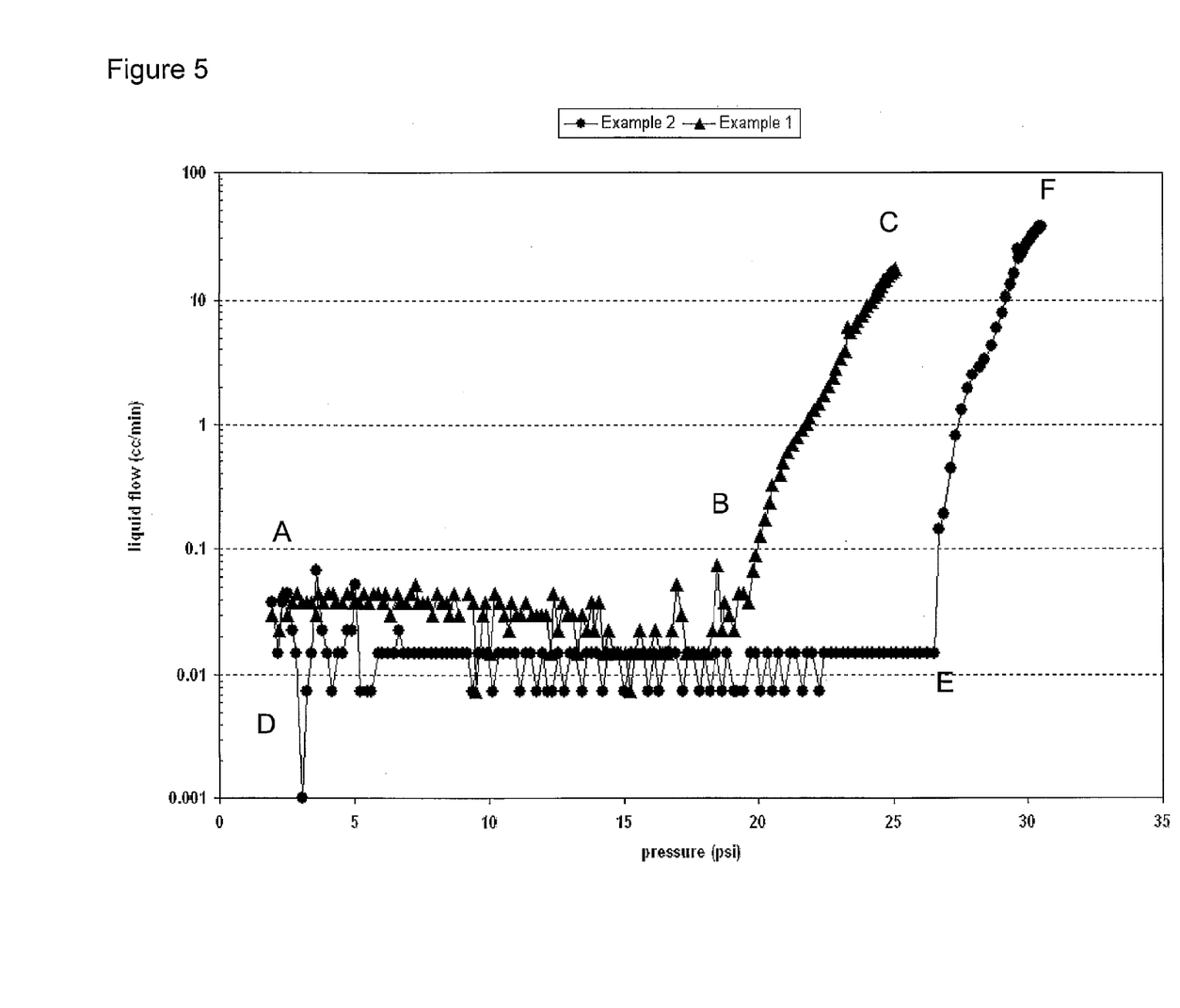
FIG. 5 illustrates the diffusive flow rate as a function of pressure for membrane disk filters as measured by the inventive method.

FIG. 5 depicts the volumetric liquid flow rate (in cc/min) as a function of pressure. As shown in FIG. 5, the region A-B shows that the flow rate through the membrane sample was very low, averaging less than 0.04 cc/min. In the region B-C, the bubble point of the sample was reached. Bulk gas flow is shown with flow characteristically increasing with pressure.

Example 2

The integrity test method of the present invention was carried out on a hydrophilic PVDF filter (rated pore size of 0.1 um, Durapore®, Millipore Corporation). The sample was wetted with IPA by circulating through the sample for about 5 minutes. As described above, the portion of the test fixture between the downstream side of the sample and the outlet was filled with IPA to create a liquid conduit. The sample was pressurized using air; Air pressure was slowly increased at a rate of 10 psi/min. The mass of IPA displaced was collected in a container and measured every 10 seconds using a balance. The mass flow rate was converted to volumetric liquid flow rate by dividing the mass flow rate by the density of IPA. FIG. 5 depicts the volumetric liquid flow rate (in cc/min) as a function of pressure. As shown in FIG. 5, the measured flow rate through the membrane sample in the region D-E was very low, on average less than 0.015 cc/min. In the region E-F, the bubble point of the sample was reached. Bulk gas flow is shown with flow characteristically increasing with pressure.

Example 3

Figure 6:
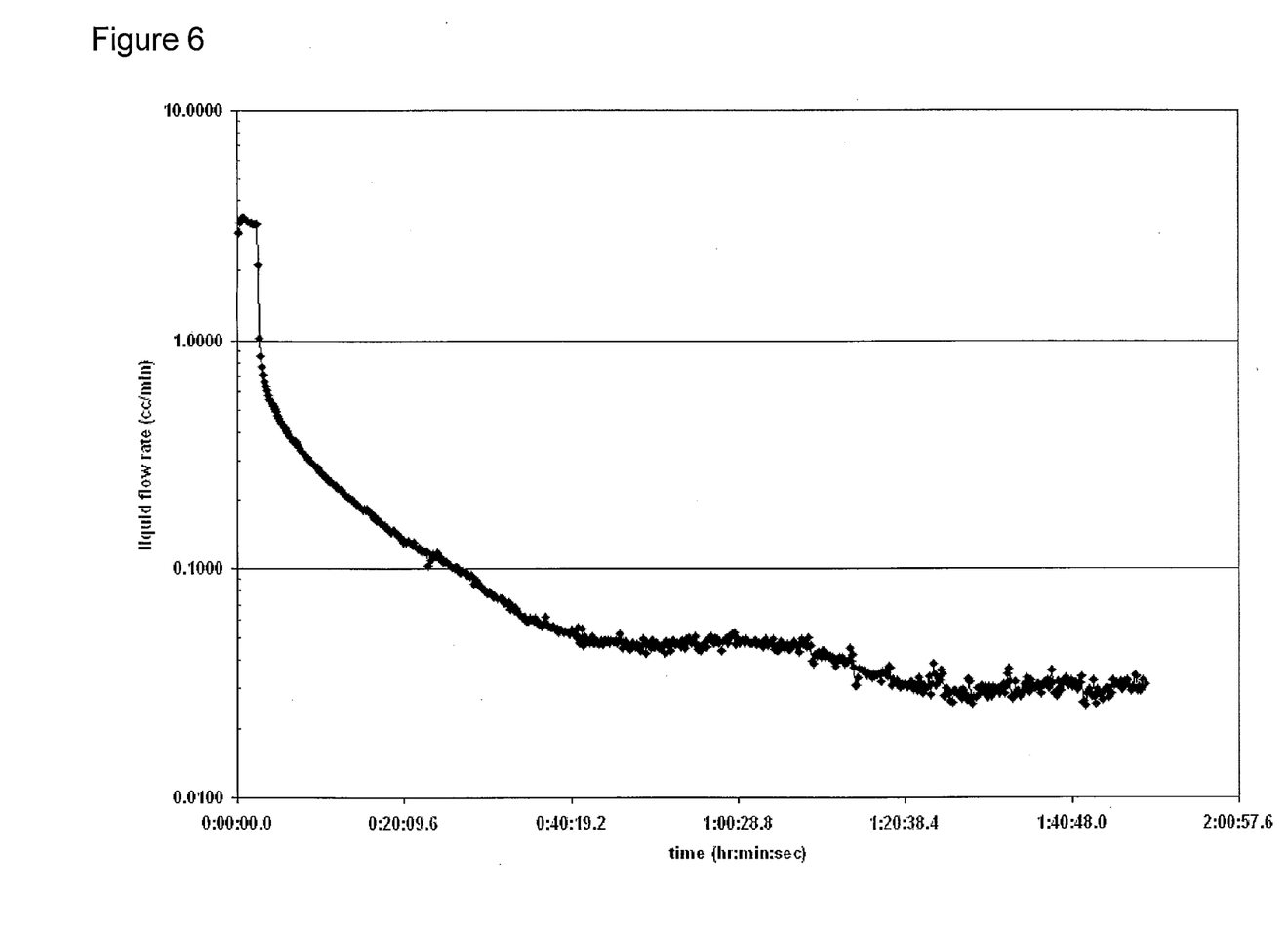
FIG. 6 illustrates the diffusive flow rate decay as a function of time for a pleated cartridge filter as measured by an embodiment of the invention.

The integrity test method of the present invention was carried out on a PVDF filter cartridge. A commercial cartridge (Durapore®, rated pore size 0.22 um, Millipore Corporation) was installed in a test fixture (Part Number CSF 786-226, Shelco Filters). The cartridge sample was wetted with IPA by circulating through the sample for 60 minutes. As described above, the portion of the test fixture between the downstream side of the sample and the outlet was filled with IPA to create a liquid conduit. The sample was pressurized using air; the air pressure was held constant at 10 psi. The mass of IPA displaced was collected in a container and measured every 10 seconds using a balance. The mass flow rate was converted to volumetric liquid flow rate by dividing the mass flow rate by the density of IPA. FIG. 6 depicts the volumetric liquid flow rate (in cc/min) decay as a function of time. As shown in FIG. 6, liquid flow rate as low as 0.03 cc/min can be measured using this technique.

Example 4

Figure 7:
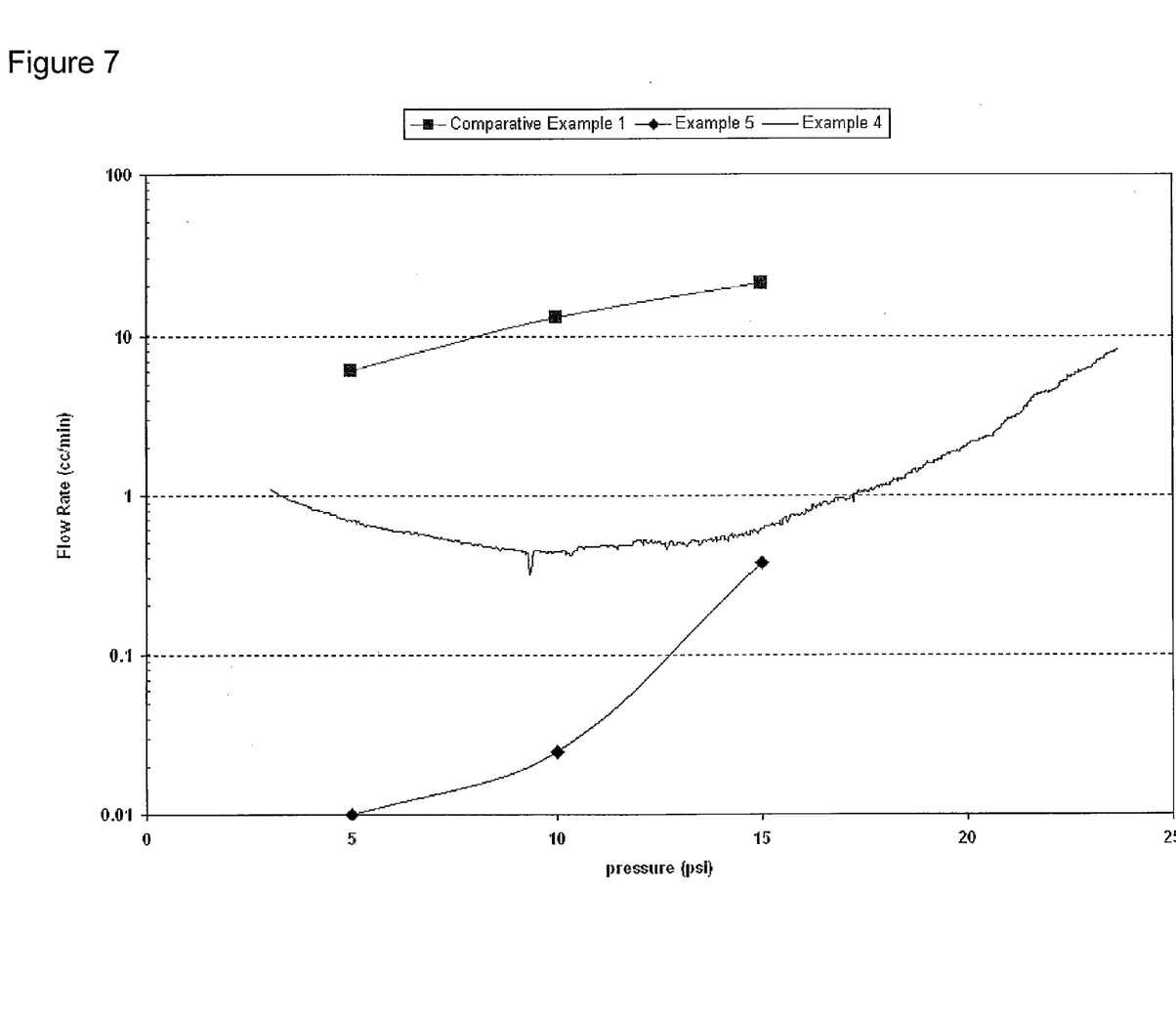
FIG. 7 shows a comparison between the gas-liquid diffusion test and the inventive method for pleated cartridge filters.

The integrity test method of the present invention was carried out on an expanded PTFE filter cartridge. A commercial ePTFE membrane, Part Number GMM 109, manufactured by W. L. Gore & Associates, Inc was sandwiched between two polypropylene backers, then pleated and converted into a 10 inch polypropylene cartridge element using methods well known in the art. The effective filtration area of the cartridge was 6.9 ft². The cartridge OD and ID were 2.45 inches and 1.65 inches respectively. The cartridge was installed in a test fixture (Part Number CSF 786-226, Shelco Filters). The cartridge sample was wetted with IPA by circulating through the sample for about 60 minutes. As described above, the portion of the test fixture between the downstream side of the sample and the outlet was filled with IPA to create a liquid conduit. The sample was pressurized using air; air pressure was slowly increased at a rate of 0.25 psi/min. The mass of IPA displaced was collected in a container and measured every 10 seconds using a balance. The mass flow rate was converted to volumetric liquid flow rate by dividing the mass flow rate by the density of IPA. FIG. 7 depicts the volumetric flow rate (in cc/min) as a function of pressure. As shown in FIG. 7, the liquid flow rate through the cartridge sample was less than 1 cc/min.

Example 5

The integrity test method of the present invention was carried out on an hydrophilic PVDF filter cartridge (Rated Pore Size 0.22 um, Durapore®, Millipore Corporation). The cartridge was installed in a test fixture (Part Number CSF 786-226, Shelco Filters). The cartridge sample was wetted with 70/30 (IPA/water) mixture by circulating through the sample for about 60 minutes. As described above, the portion of the test fixture between the downstream side of the sample and the outlet was filled with 70/30 (IPA/water) mixture to create a liquid conduit. The air pressure was slowly increased in increments of about 5 psi and held at that pressure for about 5 mins. The mass of IPA/water mixture displaced was collected in a container and measured using a balance (Model CPA324S, Sartorius Corporation) during the last minute. The mass flow rate was converted to volumetric liquid flow rate by dividing the mass flow rate by the density of IPA/water mixture. FIG. 7 depicts the volumetric flow rate (in cc/min) as a function of pressure. As shown in FIG. 7, the flow rate through the cartridge sample was less than 0.5 cc/min.

At a pressure of 10 psi, using the liquid flow rate data from this example and Comparative Example 1, the FR was calculated to be 0.00189. This FR value indicates an improvement in test method sensitivity by a factor of about 529.

Example 6

Figure 8:
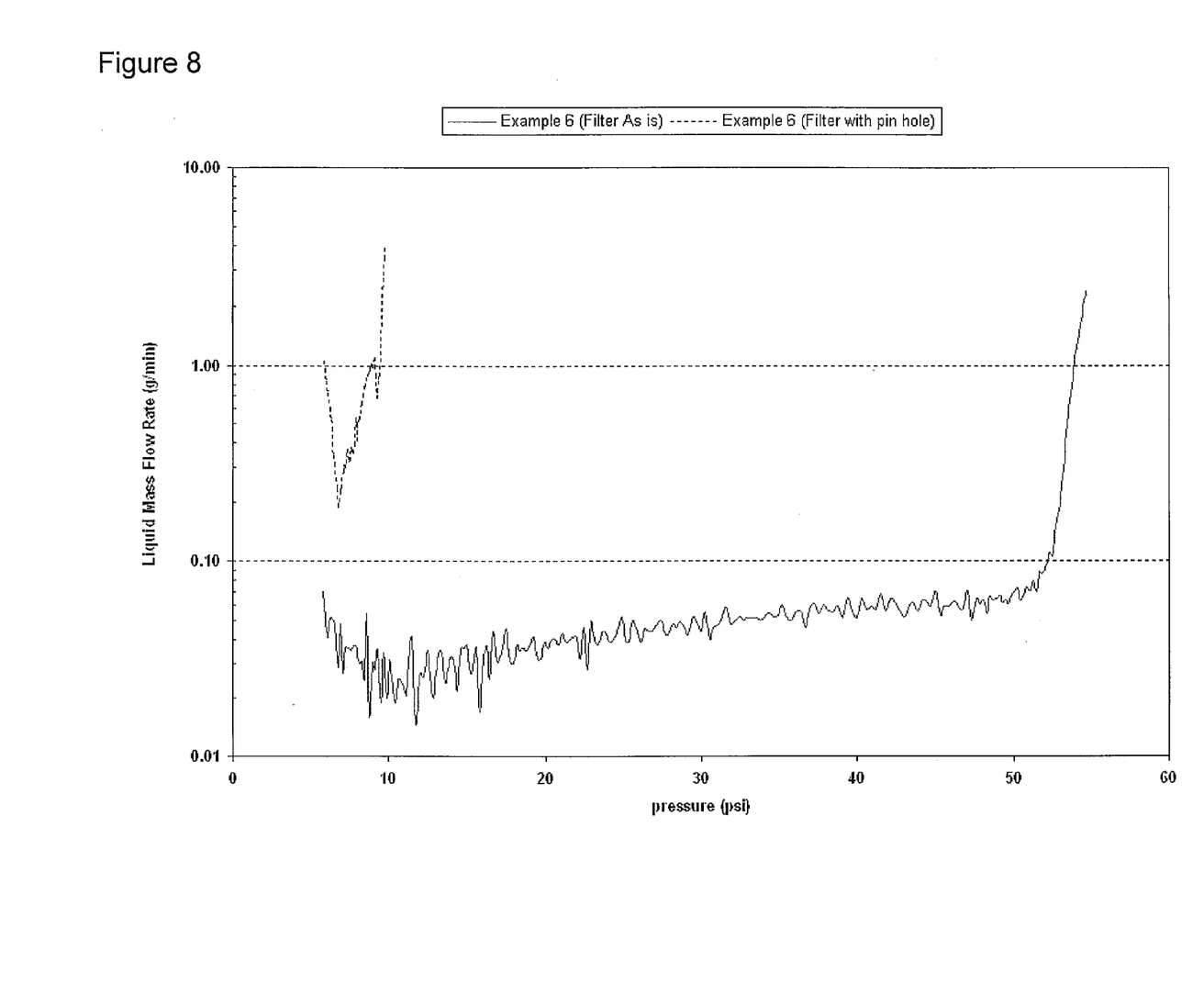
FIG. 8 shows the liquid mass flow rate as a function of pressure as measured by the inventive method for a cartridge filter with and without a pinhole.

This example illustrates the utility of the inventive method in accurately identifying a defective filter. The integrity test method of the present invention was carried out on a 0.22 µm Millipak-100 (Millipore Corporation Part # MPGL10ZW1) stacked disk filter unit comprising hydrophilic PVDF filter material. The unit was installed in a test fixture. The cartridge sample was wetted with degassed water by circulating through the unit for a few minutes. The unit was pressurized using air; the air pressure was slowly increased at a rate of approximately 2 psi/minute. The mass of water displaced was collected in a container and measured using a balance (Model CPA324S, Sartorius Corporation) continuously. The mass flow rate of water was less than 0.2 g/min for pressures up to 50 psi. As shown in FIG. 8, at a pressure of about 53 psi, the mass flow rate far exceeded 0.2 g/min illustrating that the filter had a bubble point of about 53 psi. A similar filter unit from the same lot had a Log Retention Value (LRV) of >8.9 as measured by the filter retention test.

The same filter unit was damaged by creating a single pinhole using the tip of a 10 micro liter syringe (Hamilton Part # 80030) through the vent port of the unit. Care was taken to make the defect as small as possible. The test procedure described above was repeated. As shown in FIG. 8, the mass flow rate of water exceeded 0.2 g/min even at pressure <5 psi. At a pressure of about 9.6 psi, the mass flow rate far exceeded 0.2 g/min illustrating that the filter had a much lower bubble point of about 9.6 psi, indicative of a defective filter. The LRV of the defective filter reduced significantly and was measured to be 5.9.

Particle retention by the Millipak filter cartridges was measured as follows: High purity water was circulated through the filter at a flow rate of 50 ml/min. An optical particle counter (Particle Measuring Systems LiquiLaz-S02) was included in the loop to measure particle concentrations. A suspension of 500 nm polystyrene latex particles (Duke Scientific Cat #3500A) was injected into the circulating water upstream of the filter. The injection rate was chosen to yield a particle concentration of 4.0E6/mL upstream of the filter. Measured particle concentrations downstream of the damaged and undamaged filters were 4.6/mL and <0.05/mL respectively. Calculated filter Log Reduction Values (LRVs) based on these concentrations were 5.9 and >8.9 respectively.

Example 7

Figure 9:
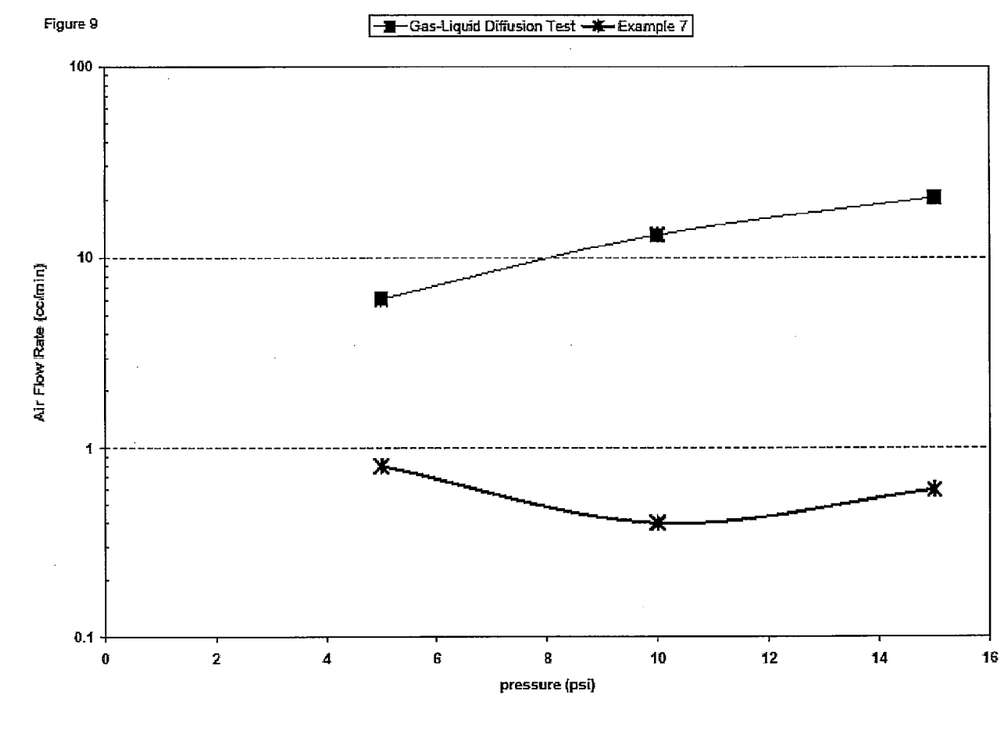
FIG. 9 shows a comparison of the diffusive flow rate between the gas-liquid diffusion test and the inventive method.

The integrity test method of the present invention was carried out on a hydrophilic PVDF filter cartridge (Rated Pore Size 0.22 um, Durapore, Millipore Corporation) according to the embodiment described in FIG. 4. The cartridge was installed in a test fixture (Part Number CSF 786-226, Shelco Filters). The cartridge sample was wetted with 70/30 IPA/water mixture by circulating through the sample for about 45 minutes. As described in FIG. 3, the portion of the test fixture between the downstream side of the sample and the outlet was filled with IPA/water mixture to create a liquid conduit of length 12" of 5/8 inch diameter followed by 28 inch length of 1 inch diameter followed by 88 inches of 1/4 inch diameter tubing. The air pressure was slowly increased and the sample was held at a given pressure for about 20 mins. The Sartocheck 4 (Sartorius AG) was used for the flow and pressure measurements. FIG. 9 shows the air flow rate as a function of pressure.

At a pressure of 10 psi, using the air flow rate data from this example and Comparative Example 1, the FR was calculated to be 0.0303. This FR value indicates an improvement in test method sensitivity by a factor of about 33.

Comparative Example 1

The standard gas-liquid diffusion test was carried out on the cartridge sample described in Examples 5 and 7. This test was performed using the Sartocheck 4® (Sartorius AG). The cartridge was installed in a test fixture (Part Number HU11U7TY00SOS, Sartorius Stedin Biotech). The cartridge was wetted with 70/30 IPA: water mixture and pressurized on the inlet side with air under a certain test pressure. The air pressure was increased in increments of about 5 psi. The gas flow on the downstream side of the filter was measured at the test pressure. FIG. 7 and FIG. 9 show the gas flow rate as a function of pressure.

The invention claimed is:

1. A method for testing the integrity of a filter comprising porous filter material having a bubble point, the method comprising:
   providing a filter fixture with an inlet for fluid flow and outlet for fluid flow;
   installing said porous filter in the filter fixture between the inlet and the outlet;
   wetting the porous filter material to fill the pores of the material with a wetting liquid;
   filling the filter fixture between the wetted, porous filter media and the fluid outlet with a liquid;
   pressurizing the filter fixture by providing gas at the fluid inlet of the filter fixture at a pressure lower than the bubble point of the wetted, porous filter;
   weighing the liquid displaced from the filter fixture responsive to the pressurizing of the filter fixture; and
   calculating the gas flow from the displaced liquid volume.

\* \* \* \* \*